US00PP09641P

United States Patent [19]

Olesen et al.

[11] Patent Number: Plant 9,641

[45] Date of Patent: Sep. 10, 1996

[54] SHRUB ROSE PLANT NAMED 'POULFAN'

[75] Inventors: Pernille Olesen; Mogens Olesen, both of Fredensborg, Denmark

[73] Assignee: DeVor Nurseries, Inc., Watsonville, Calif.

[21] Appl. No.: 414,533

[22] Filed: Mar. 31, 1995

[51] Int. Cl.[6] ..... A01H 5/00

[52] U.S. Cl. ..... Plt./1

[58] Field of Search ..... Plt./1, 22, 26

*Primary Examiner*—Howard J. Locker

*Attorney, Agent, or Firm*—Christie, Parker & Hale, LLP

[57] ABSTRACT

A shrub rose variety producing large, single, pink flowers.

1 Drawing Sheet

SUMMARY OF THE INVENTION

The present invention relates to a a new and distinct shrub rose variety which was originated by crossing as an unnamed and undistributed seedling of our creation as seed parent and 'The Fairy' as pollen parent, respectively. The varietal denomination of this new rose is 'Poulfan'.

Among the novel characteristics possessed by this new variety which distinguish it from its parents and all other varieties of which we were aware are its large, single pink flowers borne on a hardy, floriferous plant.

Asexual reproduction by budding of the new variety as performed in Watsonville, Calif., shows that the foregoing and other distinguishing characteristics come true to form and are established and transmitted through succeeding propagations. Other known forms of asexual reproduction may be also employed.

BRIEF DESCRIPTION OF ILLUSTRATION

The accompanying illustration show typical specimens of the vegetative growth and flowers of the new variety in different stages of development and depicted in color as nearly true as it is reasonably possible to make the same in a color illustration of this character.

DESCRIPTION OF THE NEW VARIETY

Parentage: Seedling.

*Seed parent.*—Unnamed, unpatented seedling.

*Pollen parent.*—'The Fairy'.

Class: Shrub.

The following is a detailed description of the new variety, from specimens grown outdoors in Watsonville, Calif., in the month of September. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

FLOWER

Blooming habit: Recurrent.

A. Bud:

(1) *Size.*—Small, about 1½ to 2 cm long by 1 to 1½ cm wide.

(2) *Form.*—Pointed, tapering.

(3) *Color.*—When sepals first divide, bud color is near 49A.

(4) *Sepals.*—Longer than bud, about 1½ cm long, spread and reflex when bloom opens; some sepals are foliaceous, leaf-shaped ends on most with small leafs protruding from sides. Color Near 146B.

(5) *Peduncle.*—Length: About 2½ to about 4 cm. Aspect: Small prickles. Strength: Erect, sturdy, Color: Near 140C.

(6) *Bracts.*—Approx. 10 per bunch on cluster; near 147A; leaf-shaped when mature, about 2 cm below calyx.

B. Bloom (1) *Size.*—Average size when fully expanded — about 5 cm to about 6 cm.

(2) *Borne.*—Mainly in clusters of about 3 to 24 blooms, most clusters 12 to 14 blooms.

(3) *Form.*—Informal, becomes flat and showing the center. A distinctive characteristic is that on fully open blooms stamens form a circle evenly spaced around styles which appear to be rising from the center giving a mushroom effect.

(4) *Petalage.*—Number of petals under normal conditions — about 5.

(5) *Color (⅓ to ½ open).*— Petals — Top surface: near 49A; Undersurface: near 49A. Base of petals — (point of attachment): Near 4D darkening to near 1B at point of attachment. General tonality from a distance Pink.

(6) *Color (fully open).*—Petals — Top surface: near 56C; Undersurface: near 56C. General tonality from a distance: Pink.

(7) *Color change.*—As bloom ages how colors change: Color lightens evenly and remains a constant color. Petal top surface: Light pink. Petal undersurface: Light pink. General tonality at a distance: Pink.

C. Petals:

(1) *Texture.*—Thick.

(2) *Appearance.*—Inside slightly velvety and outside matte.

(3) *Form.*—Elliptic with ruffled edges.

(4) *Arrangement.*—Flat.

(5) *Petaloids.*—Few, (0 to 2).

(6) *Fragrance.*—None.

(7) *Lasting quality.*—Not suitable for cut flower lasts well on plant, about 9 to 11 days.

(8) *Persistence.*—Petals drop off cleanly.

REPRODUCTIVE ORGANS

A. Stamens:

(1) *Arrangement.*—Irregularly arranged around styles, reflex back on fully open blooms.

(2) *Anthers.*—Color near 17B on outer edges, balance near 18B.

(3) *Filaments.*—Near 1B.
(4) *Pollen.*—Color — near 17B.

B. Pistils:
(1) *Styles.*—Bunched, with even length.
(2) *Stigmas.*—Color tip and base near 10B, balance near 31B.

C. Characteristics of hips: Not observed.

PLANT

A. Form: Mounds, low growing shrub, free branching.

B. Growth: Very vigorous; about 68 cm to about 89 cm in height at first season, grows to heaight of about 107 cm. to abot 124 cm. following seasons, plant is capable of obtaining a spread of about 122 cm.

C. Foliage: Compound 3 to 5 leaflets and some compound 7 leaflets.
(1) *Size.*—Small.
(2) *Quantity.*—Abundant.
(3) *Color.*—New foliage — upper side between 143A and 143B; underside near 146C; mature foliage — upper side near 147A, underside near 147B.
(4) *Shape.*—Ovate.
(5) *Texture.*—Upper side smooth; underside matte.
(6) *Edge.*—Serrate.
(7) *Serration.*—Denticulate.
(8) *Leaf stem.*—Color — medium green.
(9) *Stipules.*—Slender, small glands on edges, adnate, about 1 cm. long.
(10) *Rachis.*—Small prickles on underside
(11) *Petioles.*—Top near 146A, underside near 146C.
(12) *Auricle.*—Thin, edges tipped with glands, reflexing outward.
(13) *Resistance to disease.*—Very resistant to blackspot, slightly to mildew and very resistant to rust.

D. Wood:
(1) *New wood.*—Color near 144C, bark smooth.
(2) *Old wood.*—Color near 144B, bark smooth.

E. Flower stem: About 38 cm to about 49 cm from last cut.

F. Thorns:
(1) *Thorns.*—Quantity: On main stalk, some; laterals from stalk, average. Form: Thin, slightly curved downward, wing-shaped. Length: Medium, about 0.8 cm Color: Near 162B. Position: Predominately irregular, some pairs.
(2) *Prickles.*—None.

G. Winter hardiness: Winter hardy in Denmark and in Watsonville, Calif.

I claim:

1. A new and distinct shrub rose variety, substantially as herein shown and described.

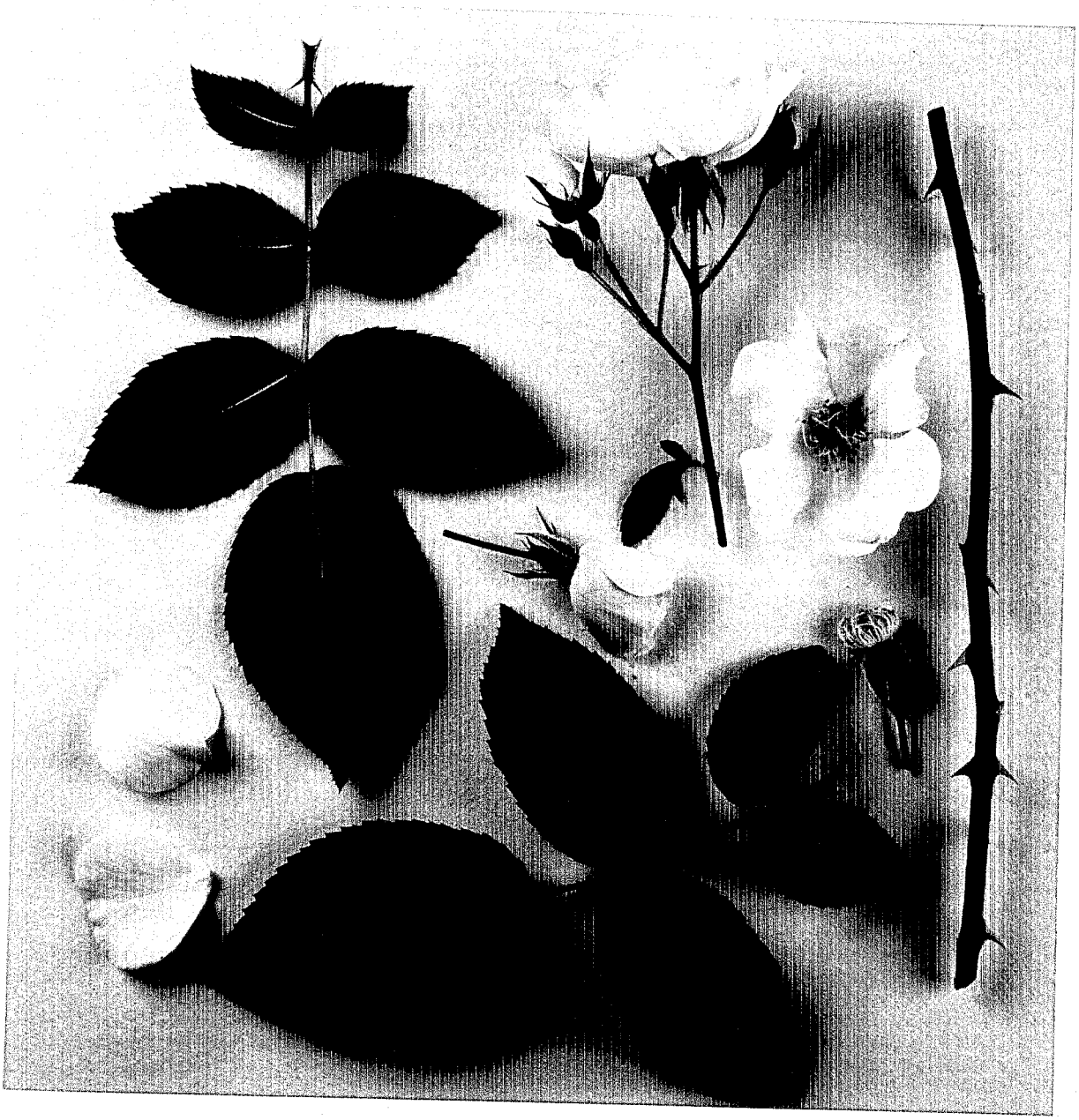

* * * * *